(12) United States Patent
Axtell et al.

(10) Patent No.: US 7,268,269 B2
(45) Date of Patent: Sep. 11, 2007

(54) MULTI-FUNCTIONAL PROTECTIVE TEXTILES AND METHODS FOR DECONTAMINATION

(75) Inventors: Holly C. Axtell, Factoryville, PA (US); Scott M. Hartley, Clarks Summit, PA (US); Robert A. Sallavanti, Dalton, PA (US)

(73) Assignee: Gentex Corporation, Carbondale, PA (US)

(*) Notice: Subject to any disclaimer, the term of this patent is extended or adjusted under 35 U.S.C. 154(b) by 458 days.

(21) Appl. No.: 10/862,992

(22) Filed: Jun. 8, 2004

(65) Prior Publication Data

US 2007/0187029 A1    Aug. 16, 2007

Related U.S. Application Data

(62) Division of application No. 10/371,810, filed on Feb. 21, 2003, now abandoned.

(60) Provisional application No. 60/360,050, filed on Feb. 25, 2002.

(51) Int. Cl.
*B32B 37/00*    (2006.01)

(52) U.S. Cl. ............... 588/299; 588/300; 588/400; 977/777; 977/779; 977/881; 156/148

(58) Field of Classification Search ............. 156/148; 588/299, 300, 400; 977/777, 779, 811, 903
See application file for complete search history.

(56) References Cited

U.S. PATENT DOCUMENTS

| | | | |
|---|---|---|---|
| 4,242,226 A | 12/1980 | Siren | |
| 4,797,318 A | 1/1989 | Brooker et al. | |
| 4,831,011 A | 5/1989 | Oikawa et al. | |
| 5,482,773 A | 1/1996 | Bair | |
| 5,486,410 A | 1/1996 | Groeger et al. | |
| 5,639,307 A | 6/1997 | Bellemare | |
| 5,712,219 A | 1/1998 | Klabunde et al. | |
| 5,736,473 A | 4/1998 | Cohen et al. | |
| 5,759,939 A | 6/1998 | Klabunde et al. | |
| 5,914,436 A | 6/1999 | Klabunde et al. | |
| 5,990,373 A | 11/1999 | Klabunde | |
| 6,024,813 A * | 2/2000 | Groeger et al. | ............ 156/62.8 |
| 6,054,488 A | 4/2000 | Oliver et al. | |

(Continued)

FOREIGN PATENT DOCUMENTS

JP          5131136          5/1993
WO     WO-01/06054 A1 *    1/2001

*Primary Examiner*—Jeff H. Aftergut
(74) *Attorney, Agent, or Firm*—Keusey, Tutunjian & Bitetto, P.C.

(57) ABSTRACT

A reactive and adsorptive (i.e., multi-functional protective) textile and methods for constructing and using same which possess at least chemically reactive and biocidal properties. Nanoparticles from different classes such as metal oxides, metal hydroxides, metal hydrates and POMs are incorporated into elements which can be utilized in a wide variety of protective materials. The nanoparticles may be treated to reduce water solubility or combined with halogens, alkali metals or secondary metal oxides to specifically engineer the nanoparticle to address a particular chemical or biocidal threat. In one aspect, a protective spatially-distributed biocidal interface is provided comprising a textile having interior structures, wherein protective nanoparticles bonded to said interior structures such that an article or portions of an article which are maintained in proximity to the textile are permitted to safely pass through a contaminated environment without dispersing the nanoparticles from protective proximity to the article.

25 Claims, 3 Drawing Sheets

U.S. PATENT DOCUMENTS

| | | |
|---|---|---|
| 6,087,294 A | 7/2000 | Klabunde et al. |
| 6,093,236 A | 7/2000 | Klabunde et al. |
| 6,113,807 A | 9/2000 | Yamaura et al. |
| 6,294,222 B1 | 9/2001 | Cohen et al. |
| 6,316,378 B1 | 11/2001 | Giebelhausen et al. |
| 6,376,404 B1 | 4/2002 | Giebelhausen et al. |
| 6,417,423 B1 | 7/2002 | Koper et al. |
| 6,607,994 B2 | 8/2003 | Soane et al. |
| 2002/0028333 A1 | 3/2002 | Giebelhausen et al. |
| 2002/0035032 A1 | 3/2002 | Koper et al. |
| 2002/0187258 A1 | 12/2002 | Bellemare et al. |

\* cited by examiner

MULTI-FUNCTIONAL PROTECTIVE TEXTILES AND METHODS FOR DECONTAMINATION

CROSS-REFERENCE TO RELATED APPLICATIONS

This is a division of U.S. patent application Ser. No. 10/371,810, filed on Feb. 21, 2003, now abandoned, which in turn claims the priority date benefit of U.S. Provisional Application 60/360,050 filed on Feb. 25, 2002.

BACKGROUND OF THE INVENTION

1. Technical Field

The present invention relates generally to protective textiles, and in particular, to reactive and adsorptive textiles for providing multi-functional protection from chemical and biological agents and methods for providing and using such textiles for decontamination.

2. Description of Related Art

Historically, activated carbon has been incorporated into textiles for clothing and into filters to provide adsorptive protection. While activated carbon is extremely effective for adsorbing toxic vapors, activated carbon imparts only partial protection against chemical agents, which are captured through physical entrapment within its pores. Since this entrapment is a physical process, activated carbon does nothing to neutralize an absorbed chemical, it simply stores it. Such storage presents a host of problems: these materials may be released over time; the carbon has capacity restrictions and thus cannot be used indefinitely; and storage results in disposal problems after usage. Finally, activated carbon does not provide protection from biological agents (such as anthrax or small pox). Previously, protection against biological contamination has been relegated to barrier methods, i.e. full body suits. In addition to the life support problems associated with hermetic sealing, these barriers present similar disposal problems after being coated with harmful entities.

To fulfill a long standing need to provide biocidal components for protective systems for military and civilian EMS applications, scientists have been developing metal-based nanoparticles. U.S. Pat. No. 6,057,488 discloses effective biocidal properties of metal-oxide nanoparticles when dispersed as a powder or combined in a test tube with biological contaminants. Due to the unique physical properties and size of nanoparticles, it has heretofore been impossible to separate and fix the nanoparticles into a tangible form that could be flexibly integrated into protective systems and combined with conventional adsorbents.

Accordingly, a need exists for an efficient and effective protective system which has biocidal properties for the destruction of biological agents in addition to reactive properties for the adsorption, decomposition and neutralization of chemical agents.

SUMMARY OF THE INVENTION

The present invention is directed to reactive and adsorptive textiles which possess chemically reactive properties, biocidally reactive properties, chemically adsorptive properties, or combinations of such properties. Advantageously, the present invention successfully overcomes significant material handling challenges and results in a system which can provide efficient and effective adsorption and neutralization of harmful chemical agents as well as biological agents in, e.g., a textile form.

The system may be combined with conventional activated carbon (e.g., in beads or powder form) to produce a protective system having enhanced chemical adsorption as well as biocidal properties.

In yet another aspect, any conventional activated carbon (e.g., in beads or powder form) which has been wettlerized may be utilized to add the ability to bind/neutralize blood agents.

In one aspect, an apparatus for protecting against chemical and biological agent threats is provided comprising a textile having interior structures, wherein protective nanoparticles bonded to said interior structures.

In yet another aspect, a protective spatially-distributed biocidal interface is provided comprising a textile having interior structures, wherein protective nanoparticles bonded to said interior structures such that an article or portions of an article which are maintained in proximity to the textile are permitted to safely pass through a contaminated environment without dispersing the nanoparticles from protective proximity to the article.

In yet another aspect, a method of protecting against a chemical or biological agent with a textile-based decontaminant is provided comprising the steps of providing nanoparticles which possess protective properties, and bonding the nanoparticles to the textile with non-occluding retaining means such that an interior of the textile is adapted to decontaminate chemical or biological agents disposed within a portion of the environment that encounters the interior of the textile.

In yet another aspect, a method of protecting against a chemical or biological agent with a textile-based decontaminant is provided comprising the steps of providing a textile having nanoparticles which possess protective properties bound to the textile with non-occluding retaining means, such that an interior of the textile is adapted to decontaminate chemical or biological agents which encounter said interior of the textile. Upon exposure of the textile to a chemical or biological threat, the threat is reduced or eliminated as the threat enters the textile.

These and other aspects, features and advantages of the present invention will be described or become apparent from the following detailed description of the preferred embodiments, which is to be read in connection with the accompanying drawings.

DETAILED DESCRIPTION OF PREFERRED EMBODIMENTS

Figure 1:
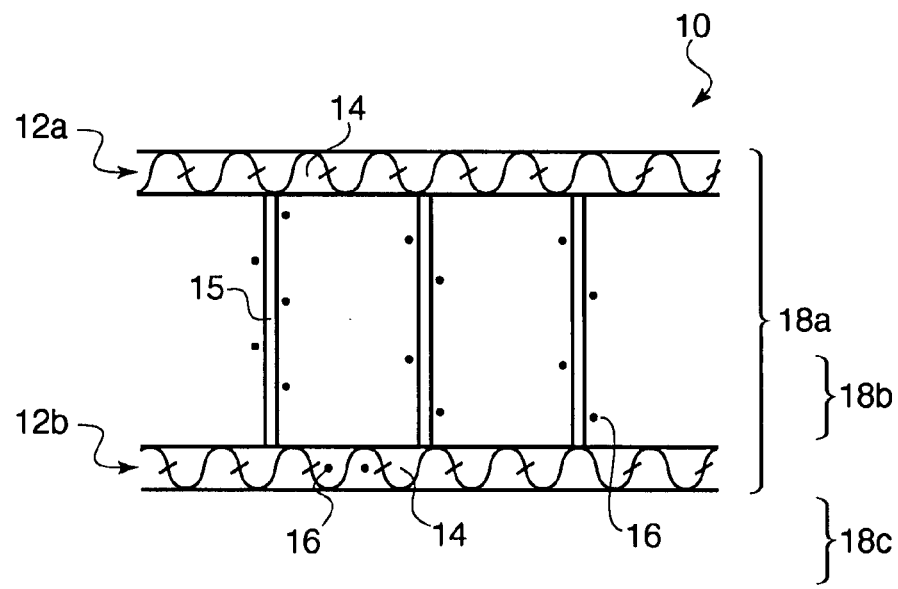
FIG. 1 illustrates an exemplary cross-sectional view of a protective textile according to an embodiment of the present invention.

The present invention comprises a textile onto which reactive/adsorptive particulates are adhered for providing a resultant protective system which has the potential to protect against both chemical and biological warfare threats. For example, these protective systems may be used to manufacture chemically and biologically protective textiles for use as clothing, shelters or air filtration. The main aspects of the present invention are listed as follows: (detailed descriptions of elements mentioned in these aspects are described further below).

According to one aspect, the present invention provides an apparatus for protecting against chemical and biological agent threats, the apparatus being comprised of a textile having interior structures, and protective nanoparticles bonded to the interior structures.

In another aspect, the present invention provides a spatially-distributed biocidal interface protective against, e.g., chemical and biological agents. This interface comprises a textile having interior structures, and protective nanoparticles bonded to the interior structures such that an article or portions of an article which are maintained in proximity to the textile are permitted to safely pass through a contaminated environment without dispersing the nanoparticles from protective proximity to the article.

It is to be noted that the nanoparticles are preferably bonded to the textile using non-occluding retaining means such that an interior of the textile is adapted to decontaminate chemical or biological agents disposed within a portion of the environment that encounters the interior of the textile. When a protective apparatus according to the present invention is exposed to a chemical or biological threat, the threat is reduced or eliminated as it enters the textile (e.g., a chemical threat is rendered inert; biological agents/entities are caused to undergo lysis and/or are prevented from reproducing). Following exposure to a threat, the protective textile may either be reused (when, e.g., nanoparticles remain unconsumed during the exposure step), or be reconditioned by bonding additional nanoparticles to the textile with further non-occluding retaining means (which may be the same or different from the non-occluding retaining means used in the initial nanoparticle bonding step).

Advantageously, when a protective apparatus/biocidal interface according to the present invention is exposed to a chemical or biological threat, such threat is reduced or eliminated as the threat enters same.

Textile Configuration Methodologies

The present invention has overcome the challenge of effectively integrating nanoparticle technology with a textile entity to produce a resultant protective system which would provide chemical and biological protection in a form which can, for example, be used independently or be incorporated for use with other materials (e.g., in layers). The resultant protective textile may, for example, be incorporated into clothing or various textile products (e.g., military apparel, filters, tents, stretchers, field equipment, blankets and other textile-based products).

It is to be noted that the textile entity used in the present invention may comprise, for example, any type of synthetic or natural fiber material (e.g., polyester, cotton, etc.) or any combination of synthetic and/or natural fibers. In one aspect, the resultant nanoparticle-treated textile can, for example, be combined into multiple layers and/or with other materials/textiles to form a multi-layered protective fabric. It is to be noted that such a fabric may be comprised of nanoparticle-treated fibers wherein the fibers themselves may be comprised of various types of materials. Preferably, textiles comprised of at least a portion of engineered fibers are used for receiving nanoparticles. These engineered fibers consist of a core material coated with a polymer having a low melting point (Tg).

It is to be noted that the challenge addressed by the present invention is partially the result of the small size of the nanoparticles themselves. Advantageously, the present invention can effectively incorporate nanoparticles into a textile entity to attain successful attachment/bonding of the nanoparticles to the textile at the necessary and effective loading and uniformity requirements while not overly occluding the nanoparticles or reducing the reactivity of the nanoparticles being attached.

A further aspect of the invention includes constructing a nanoparticular-loaded filter which can be readily combined with complementary filter media in a practical and flexible manner to address a wide variety of biological and chemical threats. In this manner, the invention represents a significant advancement in transforming nanoparticles from virtually invisible particulate matter to industrial-scale, biocidal textile-based components.

As described above, in one aspect, the textile used according to the present invention preferably comprises a textile having interior structures. These interior structures may comprise, for example, interstices of the textile. In another aspect, the interior structures comprise fibers (e.g., spacer fibers and/or non-perpendicular fibers) disposed between an upper and a lower exterior surface of the textile. Such fibers form, for example, a decontamination zone.

It is to be noted that the spacer fibers (e.g., perpendicular fibers) as well as the non-perpendicular fibers can be added between e.g., an upper and lower exterior surface of a textile in any amount/density/configuration as needed depending on the application at hand. These fibers may also comprise varying thicknesses. In addition, a length of, e.g., the spacer fibers may be adjusted to control the distance through the decontamination zone. These measures advantageously provide a variety of means for customizing/adjusting the amount of contact time with the environment and thus the level of protection provided by the resultant protective apparatus.

The present invention provides further means for customizing the level and/or type of protection provided. In one embodiment, it is to be noted that the interior structures may comprise a first layer having nanoparticles bonded thereon, wherein a second layer is added substantially parallel to said first layer to complete the protective apparatus. The second layer preferably contains activated carbon. This results in a multi-component protective system comprising a first layer for protecting against at least a biological threat and a second layer for protecting against a chemical threat. Advantageously, such a protective system boasts enhanced functionality and augmented protective capabilities (e.g., provides a way of adding additional protective capabilities to existing protective systems). Indeed, in one aspect, a nanoparticle-treated textile may be incorporated as an addendum into other materials (permeable or non-permeable), such as, e.g., other textiles, filters/filtration media, etc.

In one aspect, it is to be noted that the step of bonding nanoparticles to the textile comprises loading nanoparticles onto the spacer fibers to obtain a predetermined chemical or biological decontamination capacity. Further, the present invention involves wherein nanoparticle loading is determined to obtain a target decontamination rate based on the distance and contact time of contaminants within the environment.

Thus, in one aspect, the present invention provides an air-permeable textile having a vapor and liquid diffusion rate, wherein the diffusion rate is a function of one of textile thickness, size of spacer fibers, density of spacer fibers, configuration of spacer fibers and permeability of exterior layers.

It is to be noted that either layer may include activated carbon performance enhancing nanoparticles and/or biocidal nanoparticles, and that the textile may additionally include carbon beads having nanoparticles applied thereon. It is also to be noted that carbon and biocidal components may be placed at varying distances relative to one another in the protective system depending on such factors as the application and/or demands that the system will be subject to.

In yet another embodiment, a protective system is provided comprising a plurality of layers (e.g., textile layers) for protecting against chemical and biological agent threats which are layered to form a stack. Each of these layers may be customized as needed with appropriate types/levels of reactive/adsorptive entities (e.g., protective nanoparticles, activated carbon, iodinated resin components, etc.) attached thereon to provide protection against various types/levels/numbers of threats.

It is to be noted that the textile may further include upper and lower fabrics which bind the interior structure therebetween. These upper and lower fabrics preferably have nanoparticles applied thereon.

FIG. 1 illustrates an exemplary cross-sectional view of a protective textile 10 according to an embodiment of the present invention. More specifically, this embodiment shows wherein the interior structures comprising interstices 14 and perpendicular fibers 15 extend between upper exterior surface 12a and lower exterior surface 12b of a 3-D spacer fabric. Nanoparticles 16 are bonded to the perpendicular fibers 15, and may also be bonded to any other areas bordering the interstices 14, including an interior of the surfaces 12a and 12b. Such a configuration advantageously provides increased density and/or depth of the textile 10, thus increasing both nanoparticle loading of the textile 10 and residence time of any chemical and/or biological agents encountering the textile 10. The protective textile 10 may also include one or more optional activated carbon layers disposed at any location between the surfaces 12a and 12b (e.g., at 18a and 18b) or external to surfaces 12a and 12b (e.g., at 18c).

Figure 2:
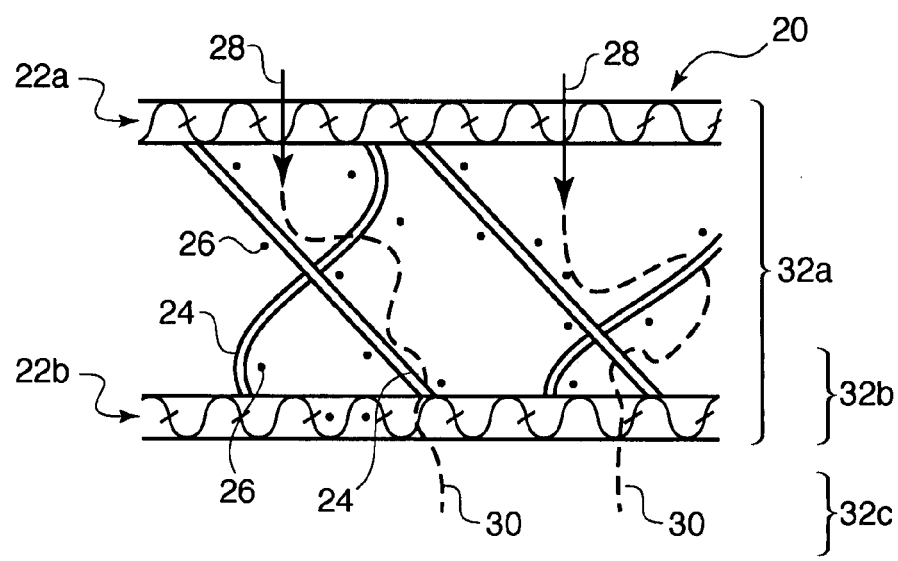
FIG. 2 illustrates an exemplary cross-sectional view of a protective textile according to another embodiment of the present invention.

FIG. 2 illustrates an exemplary cross-sectional view of a protective textile 20 according to another embodiment of the present invention. In this embodiment, the interior structures comprise fibers disposed between an upper exterior surface 22a and a lower exterior surface 22b of the textile 20, wherein the fibers comprise non-perpendicular fibers 24 which intersect direct perpendicular paths between the exterior surfaces 22a and 22b to form serpentine paths 30 through the textile. Nanoparticles 26 are preferably bonded to the non-perpendicular fibers 24, and may also be bonded to any other areas within the textile 20, including an interior of the surfaces 22a and 22b. The non-perpendicular fibers 24 cause a desirable interruption in an airflow 28 through the textile. Advantageously, the non-perpendicular fibers 24 therefore cause an increased residence time of the chemical and biological agents encountering the textile. This, in turn, increases their contact with the nanoparticles, thus resulting in increased and enhanced protective abilities.

The protective textile 20 may include one or more optional activated carbon layers disposed at any location between the surfaces 22a and 22b (e.g., at 32a and 32b) or external to surface 22b (e.g., at 32c).

It is to be noted that an additional layer comprising a substantially non-permeable material may be added to a protective apparatus/biocidal interface of the present invention. Such a layer may be added at any position/location within or external to the protective system (e.g., within the textile, between the textile and the upper and lower fabrics, or external to either/both of the upper and lower fabrics) and provides an additional barrier means for preventing, for example, the nanoparticles embedded within/onto the protective system from being overwhelmed with, e.g., a liquid or gas flow contaminant. As such, this substantially impermeable layer may or may not be added to the overall protective system depending on what particular conditions/demands it is contemplated that the system will be subjected to.

Figure 3:
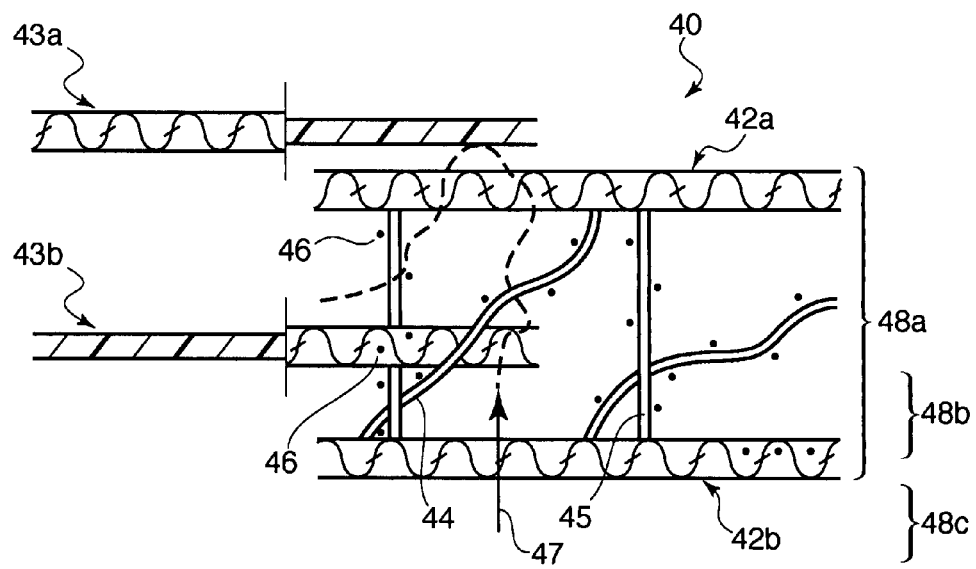
FIG. 3 illustrates an exemplary cross-sectional view of a protective textile system having an outer layer and an inner layer according to yet another embodiment of the present invention.

FIG. 3 illustrates an exemplary cross-sectional view of a protective textile system 40 having interior structures comprised of fibers disposed between an upper exterior surface 42a and a lower exterior surface 42b of the textile system 40, wherein the fibers comprise both perpendicular fibers 45 and non-perpendicular fibers 44. Nanoparticles 46 are preferably bonded to the perpendicular fibers 45 and the non-perpendicular fibers 44, and may also be bonded any other areas within the textile, including an interior of the surfaces 42a and 42b.

An optional outer layer 43a (e.g., a quarpel-treated layer which is, e.g., low-permeable) and/or an optional inner layer 43b (e.g., low permeable or non-permeable) may be included to reduce or restrict air flow 47 through the textile system 40. The "quarpel" treatment is a water and oil resistant finish. A quarpel-treated layer serves two purposes: low air permeability and greater resistance to liquids. Advantageously, this prevents the chemical agent from instantaneously soaking directly through the textile 40 and overwhelming the nanoparticles 46. As illustrated, either or both of layers 43a and 43b may be non-woven, barrier layers made from plastics material.

In addition, the protective textile system 40 may optionally include one or more activated carbon layers disposed at any location between surfaces (e.g., at 48a and/or 48b) or external to a surface (e.g., at 48c).

Figure 4:
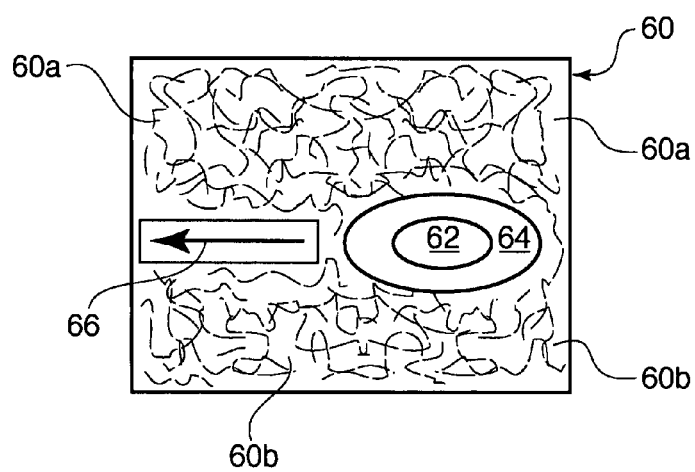
FIG. 4 is an exemplary diagram illustrating use of a protective textile as a biocidal interface according to an aspect of the present invention.

FIG. 4 is an exemplary diagram illustrating use of a protective textile as a biocidal interface according to an aspect of the present invention. In operation, the protective textile essentially acts as a biocidal interface 64 between an article 62 and a contaminated environment 60 which may contain chemical threats 60a and/or biological threats 60b. The biocidal interface 64 has, e.g., at least nanoparticles bonded thereon. Arrow 66 illustrates an exemplary passage of the article 62 enveloped in the biocidal interface 64 through/within the contaminated environment 60.

Examples of articles include at least a portion of a human, foodstuffs, a space housing a life form, etc. Preferably, the article 62 is enveloped in the protective textile or otherwise coupled to the interface prior to entering the contaminated environment. In one embodiment, the interface is air/liquid permeable. Advantageously, the present invention provides a means for allowing the article 62 which is maintained in proximity to the biocidal interface 64 (e.g., protective textile) to pass safely through the contaminated environment 60 without dispersing the nanoparticles from a protective proximity to the article 62. Additionally, the present invention provides a means for causing the nanoparticles in the biocidal interface 64 (e.g., protective textile) to remain in a substantially fixed position relative to each other.

Figure 5:
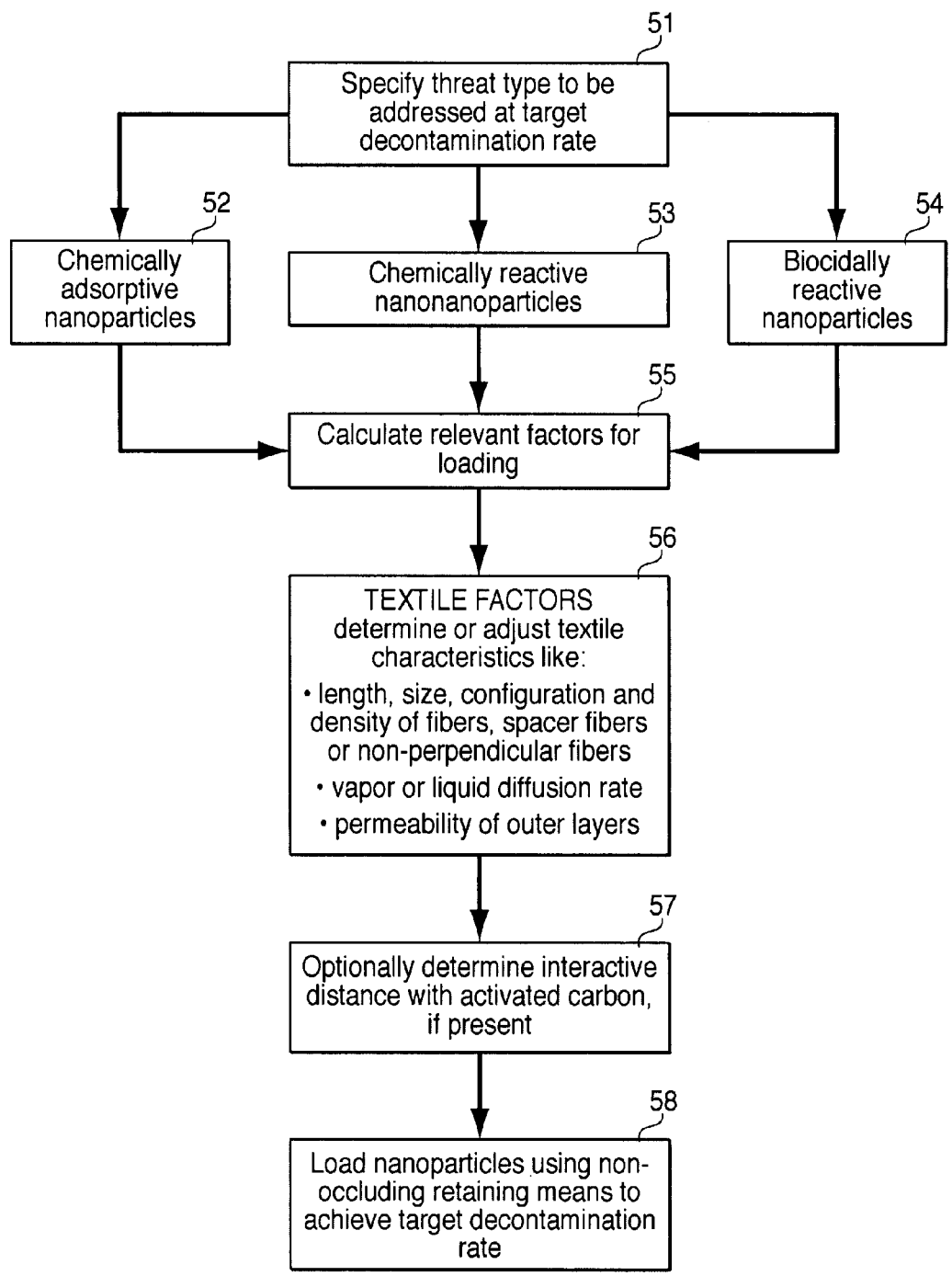
FIG. 5 is an exemplary flow chart illustrating a method of protecting against a biological or chemical agent with a textile-based decontaminant according to an aspect of the present invention.

FIG. 5 is an exemplary flow chart illustrating a method of protecting against a biological or chemical agent with a textile-based decontaminant according to an aspect of the present invention. In step 51, a threat-type to be addressed is specified at a target decontamination rate. Depending on the type of threat, any or all of the following nanoparticles may be employed: chemically adsorptive nanoparticles 52, chemically reactive nanoparticles 52 or biologically reactive nanoparticles 54. Upon determining the type(s) of nanoparticles to be employed, relevant factors for loading same may be calculated (step 55).

A textile is provided and textile factors are analyzed (step 56); such factors may comprise any of: determining or adjusting textile characteristics (e.g., length, size, configuration and density of fibers, spacer fibers and/or non-perpendicular fibers; vapor or liquid diffusion rates; permeability of outer layers). If activated carbon is present, an effective interactive distance between the nanoparticles and the carbon is determined (step 57). The nanoparticles are then loaded onto the textile preferably using a non-occluding retaining means to achieve the target decontamination rate (step 58).

Reactive Nanoparticles

The reactive/adsorptive particulates used according to the present invention are preferably inorganic, reactive nanoparticulates formed from about 1 nm to about 200 nm sized nanoparticle clusters.

Reactive nanoparticles are environmentally stable nanometer-sized clusters of atoms and molecules with high surface areas and unique morphologies which result in high chemical reactivity. Since these nanoparticles have immense surface areas, they possess extraordinary catalytic and reactive properties, which differentiate them from their bulk-chemical species relatives. In contrast to the bulk-chemical species, nanoparticles have a statistically significantly higher number of atoms/ions/molecules residing at the surface of the cluster. These reactive nanoparticles are preferably comprised of metal complexes of oxides, metal complexes of hydroxides, metal complexes of hydrates as well as polyoxometallates (POMs).

The reactive nanoparticles preferably used for protective system applications according to the present invention are specifically engineered to destructively adsorb chemicals and microorganisms. Such nanoparticles are capable of absorbing and then detoxifying hazardous chemicals by breaking molecular bonds to yield harmless end products. Similarly, such reactive nanoparticles are able to kill or inactivate microorganisms by attacking cell membranes and oxidizing important functional proteins or DNA. The nanoparticles may be enhanced or modified for environmental purposes. Thus, the nanoparticles preferably used according to the present invention include at least one of chemically adsorptive nanoparticles, chemically reactive nanoparticles, and biocidally reactive nanoparticles. Further, the nanoparticles used according to the present invention preferably have a Brunauer-Emmett-Teller (BET) multi-point surface area of at least about 70 $m^2/g$ for older nanoparticles to at least about 1200 $m^2/g$ or more for more advanced nanoparticles and have an average pore radius of at least about 45 Angstroms to at least about 100 Angstroms.

Exemplary nanoparticles which may be used include metal oxide composites in powder nanoparticulate form. These metal oxide composites comprise metal oxide nanoparticles having oxygen ion moieties on their surfaces with reactive atoms interacted or chemisorbed with those surface oxygen ions. For example, the metal oxide nanoparticles may be taken from the group consisting of oxides of Mg, Ti, Ca, Al, Sn, Fe, Co, V, Mn, Ni, Cr, Cu, Zn, Zr, or mixtures thereof. For example, the metal oxide nanoparticles may comprise MgO, $TiO_2$, CaO, $Al_2O_3$, $SnO_2$, $Fe_2O_3$, FeO, CoO, $V_2O_5$, $MnO_3$, NiO, $Cr_2O_3$, CuO, ZnO, $ZrO_2$ and mixtures thereof. Nanoparticles made of metal complexes of hydroxides, metal complexes of hydrates as well as polyoxometallates (POMs) are also suitable.

Some of the nanoparticles listed in this paragraph may also be further processed, for example to include reactive halogen atoms, alkali metal atoms, metal nitrates, $SO_2$, $NO_2$, ozone, or a second different metal oxide. Alternate processing can provide a protective coating to the nanoparticles which are not soluble, thus rendering them waterproof. These advanced processing steps are disclosed in the following U.S. Pat. Nos. 6,057,488 and 5,914,436 and 5,990,373 and 5,712,219 and 6,087,294 and 6,093,236 and 5,759,939 and 6,417,423 and published U.S. Patent Application 2002/0035032 the complete disclosures of which are incorporated herein by reference thereto. Any of these products may be incorporated into the multi-functional protective products according to an aspect of the present invention.

These various classes of nanoparticles have been noted for their ability to chemically decompose classical chemical warfare agents as well as many of the toxic industrial chemicals (TICs) and toxic industrial materials (TIMs). The reactive nature of the interaction breaks molecular bonds to reduce chemical species to non-toxic by-products. For example, nanoparticles have been shown effective in chemical destruction of carbon tetrachloride ($CCl_4$), dimethyl-methyl-phosphonate (DMMP), paraoxon (as simulant for VX and GD), 2-chloroethyl-ethyl sulfide (2-CEES, one-armed Mustard), military agents and acid gases.

Compared to activated carbon, studies have proven that nanoparticles have a much higher capacity to inactivate chemical warfare simulants. More specifically, nanoparticles chemically decompose mustard (HD) agent, as indicated by the presence of 1,4-Dithiane, a known HD degradation product. In certain instances, the nanoparticles perform the same or better than activated carbon, but in lighter weight materials with more compact volumes.

In providing biological protection, the protective fibers provide protection against biological warfare agents or infectious microorganisms such as, e.g., viruses, (vegetative) bacteria, sporulated bacteria (Anthrax), fungi or protozoa. Utilizing different mechanisms, the reactive nanoparticles instantaneously attack the cell wall, proteins and DNA of the microorganisms, thereby destroying them.

It is to be noted that the term "harmful entities" as used in the present application is defined to include all biological agents and chemical agents described above, singly or in combination.

Additional Activated Carbon Components

The agents of biological warfare can be bacteria, viruses, fungi or spores, wherein some species of spores generate as dormant seeds or genetic progenitors of themselves. These species' principal difference from chemical agents is size, wherein they may measure tenths of microns up to micron size or larger, which can be at least about a thousand times larger than chemical agent species. The pores of activated carbon cannot absorb these entities which are much larger than the pores themselves. The initial wave of these biological entities rapidly blocks the outer pores of the activated carbon thereby preventing the absorption of smaller chemical species that would otherwise be easily trapped within the pores. When a contaminated environment first encounters a network of fibers containing nanoparticles, any biological agents/entities contained therein will be caused to undergo lysis. The by-products of lysis are chemical toxins more readily absorbed by the downstream activated carbon. Thus, a multi-component protective material containing biocidal nanoparticles can improve the efficacy of activated carbon in environments containing both chemical and biological warfare agents.

While any type of carbon may be used with the present invention, an activated carbonaceous bead (CarboTex bead) with an extraordinarily high surface area (e.g., about 1500 $m^2/gm$) and extraordinary hardness (e.g., from about 2 to about 10 times harder than Rohm & Haas and Kureha beads) comprises the activated carbon bead preferably used according to an aspect of the present invention. The materials and methods used for manufacturing the preferred activated carbon bead used in the present invention are described in published U.S. Patent Application No. 2002-0028333 entitled "Spherical High Performance Adsorbents with Microstructure" by Giebelhausen et al. filed on Mar. 8, 2001, U.S. Pat. No. 6,376,404 entitled "Process for the Production of Shaped High-Performance Adsorbents" by Giebelhausen et al. filed on Mar. 15, 2000, and U.S. Pat. No. 6,316,378 entitled "Process for the Production of Shaped Activated Carbon" by Giebelhausen et al. filed on Mar. 15, 2000, the disclosures of which are all incorporated herein by reference thereto.

It is to be noted that in an alternate embodiment, an activated carbon bead which has been loaded with metal ions (e.g., wettlerized) to further impart reactive properties onto the activated carbon for providing protection against blood agents which are in contact therewith, may be used.

Additional Iodinated Resin Components

Iodinated resin is used in filters for air and water purification. It is a micro-biocidal agent that consists of iodine fixed to an ion exchange resin matrix. When a microorganism contacts the ionidated resin, iodine is released. Depending upon the type of microorganism, the iodine may oxidize the cell membrane, vital proteins or DNA, thereby killing it or rendering it incapable of reproduction. Iodinated resin has biocidal efficacy against viruses, bacteria, sporulated bacteria, fungi and protozoa. Iodinated resin is typically sold in bulk in bead, fragment or powder form. Triosyn® resin is one example of a type of iodinated resin preferably used in the present invention. Such iodinated resin may be combined with the nanoparticles.

Attachment Methodologies

Depending on a given application and desired protection level, activated carbon could be contained within the same textile layer as the biocidal nanoparticle, or contained in an adjacent layer or further spaced therefrom. Spacing out the layers provides greater residence time of an ambient airflow, while compressed layers provide thinner, lighter protective materials. The iodinated resin and activated carbon powders could be attached to a textile according to any of the following exemplary methodologies.

Squeeze-Coating—This method of lamination can utilize, e.g., a Fuller Apparatus. In a preferred embodiment, this apparatus is used to completely wet a textile (for example polyester) with an adhesive via a dip tank and then to squeeze the excess out with a nip roll. Once the excess adhesive is removed, powders are then applied via, for example, a shaker system onto a wet or partially cured textile. The textile is then thoroughly cured followed by vacuuming or forced air to remove any extraneous powders from the surface of the textile. In an alternate embodiment, the adhesive (for example urethane or acrylic powders) are combined into a slurry and then passed through the Fuller Apparatus.

Pre-Pregging—Pre-pregging involves pre-impregnating a textile (for example, polyester) with a resin or adhesive prior to additional lamination. The textile is first completely coated with an adhesive and then nip-rolled to remove the excess. Preferred adhesives should possess the ability to become tacky/molten upon the application of heat after they have been pre-pregged, while at room temperature the pre-pregged materials should remain dry and non-tacky. Exemplary adhesives include a urethane-based adhesive with about 20% to about 25% solids or a hot-melt thermoplastic adhesive having about 30% solids. After coating with an adhesive, the textile is subsequently dried until it is no longer tacky. The textile coated with the dried adhesives is then considered "pre-pregged." Powders are then applied onto the pre-pregged textile, which is then quickly heated for a short period of time. Since the adhesive becomes tacky with the application of heat, the powder become permanently bonded to the adhesive. The textile is then cooled, thus rendering the adhesive non-tacky once again. Finally, to remove any extraneous powders, the resultant textile can be flushed with forced air.

Hot Melt—Hot Melt technology utilizes textiles comprised of thermoplastic polymers that are solid at room temperature. These polymers are then heated to their molten form at which time different types of materials can be adhered onto the polymer. The polymers are then set by simple cooling rather than by chemical curing or through evaporation of a solvent, which advantageously makes them more environmentally sound. Hot melt technology can be broken down into two groups: (i) Engineered Fibers; and (ii) Hot Melt Adhesives.

Engineered fibers are fibers coated with a polymer which has a lower melting point that is designed to melt away or become molten. Exemplary hot melt fibers have exteriors made of reinforced or unreinforced thermoplastics such as polyester, polyamide and ethylene vinyl acetate (EVA). Typically, engineered fibers are available in various diameters; it is to be noted that any diameter size may be utilized in the present invention. These engineered fibers can be incorporated into, for example, woven or non-woven substrates to form fabrics. Once molten, the exterior of the engineered fiber can be used as an adhesive to bond materials such as, for example, other fiber, fabrics or particulates. This results in a clean, efficient and highly controllable application of, for example, particulates in comparison with most other application methods (e.g., squeeze-coating).

Hot Melt adhesives are 100% solid thermoplastic adhesives; exemplary types which may be utilized in the present invention are EVAs, polyolefins, polyamides and other suitable adhesives. These adhesives may be applied via heat generating equipment through the use of, for example, hand-held equipment or bulk systems which reduce the solid adhesive to a molten state. The adhesive is then cured by cooling which causes it to form rapid durable double bonds across most substrates. For example, hot melts may be specifically formulated to bond to different substrates.

There are numerous advantages to using hot melt adhesives. For example, since hot melt adhesives are 100% solid systems, this reduces transportation and storage problems. In addition, the instantaneous bond strength supplied by these adhesives allows for faster and more efficient production. Indeed, in comparison with water or solvent-based adhesives, hot melts form strong bonds almost instantaneously and thus reduces the size and amount of equipment used for processing. The reduction in equipment is due to the fact that drying or curing ovens are not required. Further, the high viscosity of hot melt adhesives as compared with solvent-based systems allows them to be used on various porous and non-porous substrates without sacrificing bond strength. Finally, since hot melt adhesives do not set by means of solvent evaporation, they are considered environmentally friendly, which has become increasingly critical in light of more stringent environmental guidelines.

In one embodiment, a powder made from a hot melt adhesive is used to attach activated carbon powder onto a textile. To permanently attach the powder onto e.g., the spacer fabric, the textile is pre-impregnated or "pre-pregged" with the hot melt adhesive. If the hot melt adhesive is a fine powder, this can be done, for example, by simply sprinkling it onto the surface of the fabric, thus coating the textile. The powder-coated textile is then heated to affix the adhesive powder.

To obtain an even distribution and to facilitate ease of handling, it is to be noted that hot melt powder adhesive and/or powders can alternatively be applied via the electrostatically fluidized bed technology (discussed further in Part 2 below). Any un-bonded or extraneous powder and/or adhesive powder may be removed by flushing with forced air.

Electrostatic Attachment

An alternate method for attaching powders onto the surface of a textile involves electrostatic attachment. In one embodiment, electrostatic attachment utilizes electrostatically charged fluidized bed technology as well as a powder management system to apply powders to various textiles, without the use of adhesives or binders (e.g., activated carbon powder, iodinated resin powder, etc.) While in the present invention, this process of incorporating powdered particulates is used for textiles, it is to be noted that the electrostatic attachment method could also be used for coating particulates on barrier non-wovens, films or membranes.

In the electrostatic fluidized bed process, particulates are aerated in a fluidizing chamber and are electrostatically charged by ionized air. As the particulates become charged, they repel each other. The particles rise above the fluidizing bed, forming a cloud of charged particles. A textile is then introduced to the cloud of electrostatically charged particulates (e.g., conveyed through it). The charged particulates are attracted to and become attached to the textile, thus coating it. Since the particulates are more attracted to exposed areas than to areas which are already coated, this provides a uniform coating of powder onto the textile. Advantageously, the electrostatic fluidized bed process provides uniform powder depositions which can be adjusted to increase or decrease particulate add-on. The coating thickness and the deposition weight can be controlled by adjusting the applied voltage to the charged media as well as the exposure time of the textile to the cloud of charged particles.

Further details about the electrostatic fluidized bed process are set forth in the following U.S. patents, the complete disclosures of which are incorporated herein by reference. The references are U.S. Pat. Nos. 4,797,318 and 5,639,307 and 6,294,222 and 5,486,410 and 5,736,473 and 5,482,773 and 6,024,813 and published U.S. Patent Application 2002/0187258. Details about the electrostatic fluidized bed process are also described in foreign patent JP513 1136, the complete disclosure of which is incorporated herein by reference.

Issues that were addressed by the present invention in incorporating powder onto textiles via electrostatic attachment include:

(a) establishing the best process parameters for the equipment utilized for electrostatic attachment, (b) selecting ideal substrates for capturing the powders to obtain target loadings of nanoparticles, (c) optionally, pretreating the textile with an adhesive enhancer or binder, (d) developing a method for permanently attaching the powder after they have been electrostatically attached, and (e) for enhanced adhesion, optionally down-select a chemical adhesive to improve the attachment of the particles to the textile.

Examples of Biocidally Reactive Enabled Textiles

While a variety of attachment methodologies have been disclosed for the attachment of resin powders and activated carbon powders, the attachment methods for nanoparticles requires the balancing of numerous special conditions. The successful implementation of these requirements is collectively referred to as "non-occluding retaining means". We define "non-occluding retaining means" as a modification or control of an attachment process which optimizes certain of the below listed factors to transfer the adsorptive and reactive properties of the free-flowing nanoparticles into a textile. An exemplary listing of those factors is as follows: maintaining spatial distance between nanoparticulate clusters to avoid occlusion by clumping; matching the nanoparticle to the textile and to the attachment mechanism to insure compatibility; downselecting an adhesive (e.g. with lowest possible Tg) to avoid physically overwhelming the nanoscale sized particles by a melt flow; to maintain the characteristic nanoparticulate matter structure where a huge portion of the atoms and ions exist at the surface of the nanoparticle even with low rates of agglomeration into popcorn-type clusters; avoiding changes which would erode the surface structure consisting of jagged edges of the atoms/ions which facilitates lysis; and avoiding chemical changes and reactions which would adversely compromise adsorption of chemical entities and reactivity/adsorption toward biological and chemical entities.

While an adhesive may also be used in conjunction with electrostatic attachment, successful bonding of the nanoparticles to a substrate can be achieved via electrostatic attachment alone without any use of additional adhesives. Advantageously, the lack of additional adhesives eliminates the possibility of any unwanted chemical reactions between the adhesives and the nanoparticles in the final product, while simultaneously preventing the over-occluding of the nanoparticles, which would render them unreactive.

In one embodiment, the method of electrostatic attachment can be used to attach nanoparticles to textiles comprised of synthetic, bi-component (or multi-component) fibers. Bi-component fibers are comprised of, for example, at least two or more different types of polymers. The polymers may comprise, e.g., polyolefins, polyamides and polyesters. For example, each bi-component fiber may have an inner core comprised of polyester and an outer sheath comprised of a polypropylene or nylon depending upon the properties desired. According to this embodiment, agglomerated nanoparticles are introduced into a fluidizing bed device which uses an electromagnetic/electrostatic mechanism for vigorously impelling the charged nanoparticles onto a bi-component fiber. Once the particulates are spatially distributed onto the surface of the bi-component fiber, heat may optionally be applied, in a carefully controlled manner to permanently affixing the particulates. Under microscopy the nanoparticles can be seen to be imbedded in the low Tg thermoplastic fibers. Thus, the polymer of the fiber acts as its own adhesive. Advantageously, this method eliminates the necessity of using of additional adhesives and thus minimizes particulate over-occlusion, unwanted chemical reactions or unintended adsorption from vapors produced during adhesive curing.

Following the non-occluding retention of the particulates, it is to be noted that forced air can be used to remove extraneous particulates that were not bonded to the textile. A resultant textile treated in this manner would advantageously be able to provide biocidal capability in, for example, a textile construct (e.g., clothing, tents, apparel, etc).

Test Data

The chemical agent testing was performed by Calspan University of Buffalo Research Center (CUBRC). The samples were went to CUBRC to be challenged against Liquid/Vapor (L/V) and Vapor/Vapor (V/V) of Mustard (HD) and Soman (GD). The samples were tested in accordance to CUBRC's Standard Operating Procedure, "SOP-AEC-CHEM2-R00", which consists of a modified version of the procedures described in CRDC-SP-84010, "Laboratory Method for Evaluating Clothing Systems Against Chemical Agents—Mo Jo Waters Method," June 1984.

The samples were challenged at an ambient temperature (~23° C.) and 50% relative humidity. Each sample swatch size was 11.4 $cm^2$.

The test results shown are of samples utilizing a cover fabric comprising a nylon/cotton (50/50) "Ripstop" material. This fabric is a wind resistant nylon/cotton poplin that has been "quarpel" treated. The "quarpel" treatment is a water and oil resistant finish. The cover fabric serves two purposes: low air permeability and greater resistance to liquids. It prevents the chemical agent from instantaneously soaking directly through the fabric and overwhelming the nanoparticles.

Depending upon the agent tested, each sample was challenged with ten (10)-1 μL droplets of MeS, HD or GD, which results in a contamination density of 10 $g/m^2$. The challenge agent was applied to the outer surface of the cover fabric. All samples were tested in triplicate and each sample type included one control sample. The control sample did not contain the reactive-/adsorptive component. A complete list of test parameters is listed is Table 1.

TABLE 1

MeS, HD & GD Test Parameters

| | Liquid/Vapor | Vapor/Vapor |
|---|---|---|
| Agent: | HD & GD | HD & GD |
| Challenge: | 10 g/m2 | HD = 20 g/m3, GD = 10 g/m3 |
| Temperature: | Ambient | Ambient |
| Relative Humidity: | 50% | 50% |
| Test Duration: | 8 hours | 24 hours |
| Flow Rates: | 1 L/min (top & bottom cells) | 1 L/min (top & bottom cells) |
| Sample Size: | 11.4 $cm^2$ | 11.4 $cm^2$ |
| Polyethylene Film: | No | No |

High loft filtration media are non-wovens comprised of synthetic bi-component fibers. Bi-component fibers are made of 2 or more polymers (can have inner/outer cores). The filtration media samples were all tested with the quarpel-treated cover fabric described above.

The high-loft filtration media sample loaded with MgO nanoparticles performed very well compared to the samples without the MgO nanoparticles (control). In the MeS challenge (the results of which are shown in Table 2 below), the test sample had an MeS average permeation rate at 1 hour of only 31.9 nm/min/$cm^2$ as opposed to 324.0 nm/min/$cm^2$ for the control sample.

TABLE 2

Liquid/Vapor MeS Permeation Results

| Sample ID | Control Sample ID | Method of Attachment | MgO Add-on Wt ($g/m^2$) | CONTROL MeS Permeation Rate at 1 hr (ng/min/$cm^2$) | MeS Avg. Permeation Rate at 1 hr (nm/min/$cm^2$) |
|---|---|---|---|---|---|
| 08301-Loaded | High Loft Filtration Media | Electrostatic | 41.23 | 324.0 | 31.9 |

Table 3 shows the results of the liquid/vapor HD permeation tests with high-loft filtration media loaded with MgO nanoparticles. Surprisingly, these test samples were capable of reducing the cumulative mass of HD by up to 85%.

TABLE 3

Liquid/Vapor HD Permeation Results

| Sample ID | Sample Description | Nanoparticle Lot # | MgO Loading ($g/m^2$) | Sample Control ID | Control (μg/$cm^2$) | Sample (μg/$cm^2$) | Reduction in Cumulative Mass % |
|---|---|---|---|---|---|---|---|
| 112901-22 HLLOADED Electrostatic Attachment | High Loft Filtration Media | LH-100401 (coated) | 42.33 | Yellow-Blank Substrate | 49, 51 Mean: 50 | 8, 12, 5 Mean: 8 | 85 |
| 112901-32 HLLOADED Electrostatic Attachment | High Loft Filtration Media | 01092001P1 (uncoated) | 26.67 | Yellow-Blank Substrate | 49, 51 Mean: 50 | 28, 14, 16 Mean: 19 | 61 |

Table 4 shows a description of a sample tested against not only HD but also the live chemical agent soman (GD) which is a fluorinated organophosphorous compound that is volatile liquid. The test results for this sample in the HD and GD challenges are shown in Tables 5 and 6.

TABLE 4

Sample Description

| Sample ID | Sample Description | Nanoparticle Lot # | Nanoparticle Loading (g/m$^2$) | Sample Control ID |
|---|---|---|---|---|
| 021902-7 Electrostatic Attachment | High Loft Filtration Media | TiO$_2$ 07-0009 | 87.0 | High Loft Filtration Media |

TABLE 5

Results for HD Liquid/Vapor Testing
HD Cumulative Mass Summary, μg/cm$^2$

| | Sample 021902-7 | Control Filter Media Substrate | % Reduction in Cumulative Mass |
|---|---|---|---|
| Rep 1 | <3.93 | 33.7 | 86 |
| Rep 2 | <5.36 | 28.0 | |
| Rep 3 | <4.14 | N/A | |
| Mean | <4.48 | 30.9 | |

TABLE 6

Results for GD Liquid/Vapor Testing
GD Cumulative Mass Summary, μg/cm$^2$

| | Sample 021902-7 | Control Filter Media Substrate | % Reduction in Cumulative Mass |
|---|---|---|---|
| Rep 1 | <0.09/<0.08 | 28.9/29.4 | 99.8 |
| Rep 2 | <0.05/<0.04 | 32.8/33.1 | |
| Rep 3 | <0.03/<0.034.14 | N/A | |
| Mean | <0.06/<0.054.48 | 30.9/31.3 | |

Advantageously, the sample 021902-7 is capable of reducing the cumulative mass of HD by 86%, and is capable of reducing the cumulative mass of GD by 99.8%.

As far as trends, the data in Tables 4-6 above indicate a direct correlation of nanoparticle loading to HD or GD adsorption. Namely, the higher the nanoparticle loading on the filter media, the more HD or GD that was adsorbed.

CUBRC also performed permeation testing on textile samples following CUBRC's Standard Operating Procedure, "SOP-AEC-CHEM2-R00," which consists of a modified version of the procedures described in CRDC-SP-84010.

This testing consisted of liquid contamination/vapor penetration at ambient temperature (~23° C.) and 50% relative humidity. Samples sized at 11.4 cm$^2$ were challenged with 9 μL droplets of chemical agent HD resulting in a contamination density of 10 g/m$^2$. The sample were contained in liquid permeation cells (CRDC-SP-84010 specifications) and they did not have polyethylene film placed beneath them. Environmentally controlled air flowed across the upper and lower surfaces of the samples at ~0.9 slpm for a period of eight hours.

Analytical quantification of penetrated HD was carried out by two MINICAMS® (Miniature Chemical Agent Monitoring System) configured with Stream Selections Systems (SSS's) which are sequencing multi-port valves each capable of sampling twelve locations sequentially. The SSS's alternated between sampling the effluent of test articles and of lab air blanks. The use of blanks between samples allowed the MINICAMS® to reduce residual HD within the instrument following samples of high concentration levels.

The sample tested was a textile which contained a reactive-adsorptive component. The sample was tested in triplicate and included a control sample (which did not contain the reactive/adsorptive component). The sample included a cover layer consisting of the nylon/cotton (50/50) "Ripstop" fabric mentioned above. The HD was not applied to the outer surface of the cover fabric. The impregnated layer for the sample shown (112901-22HLLOADED) and its associated control sample was white on one side and yellow on the other. This was oriented with the white side placed downward from the outer surface. A summary of the test results is shown in Table 7. As can be seen from the results, there was a reduction in cumulative mass of 83% by the tested sample when compared to its control.

TABLE 7

HD L/V Permeation Testing
10 g/m$^2$ HD L/V Permeation Testing
(Cumulative Mass at 8 hrs, micrograms per square centimeter)

| Sample 112901-22HLLOADED | | Control Yellow-Blank Substrate | | Reduction in Cumulative Mass, % |
|---|---|---|---|---|
| Rep 1 | 8 | Rep 1 | 49 | 83 |
| Rep 2 | 12 | Rep 2 | 51 | |
| Rep 3 | 5 | | | |
| Mean | 8 | Mean | 50 | |

The nanoparticles used in accordance with the invention are those that possess a protective property, i.e. protective nanoparticles or protective nanoparticulate entities. For purposes of this application, the term "protective nanoparticles" encompasses one or more of the following three particular types of nanoparticles: chemically adsorptive nanoparticles; chemically reactive nanoparticles; and biocidally reactive nanoparticles.

Protective nanoparticles are metal-containing nanoparticles or metal-containing nanocrystals. The metals are present as metal oxides, metal hydroxides, metal hydrates, POMs. To enhance their protective properties, such metal-containing protectants may be combined with one of more of a metal oxide, Group I metals, Group IA metals, a reactive halogen, a metal nitrate, $SO_2$, $NO_2$, or ozone.

It should be noted that a bulk metal-containing particle that is ground down to a powder will not possess the protective properties of the nanoparticles used according to the invention because the ground powder will have conventional surface features. In order to distinguish powders from nanoparticles which may be seemingly in the same size range, the protectants according to the invention are referred to as finely divided nanoparticles or finely divided nanocrystals. Protective nanoparticles are formed from 1 nm to 200 nm sized nanoparticulate clusters. These clusters cling together due to van der Waals forces and therefore have many distinguishable constituent parts. A ground powder is just a single entity, with a uniform exterior surface. In contrast thereto, when the nanometer sized clusters cling together much of their original surface area is preserved providing Brunauer-Emmett-Teller (BET) multi-point surface areas of at least 70 m$^2$/g for early protective nanoparticles and surface areas of at least 1200 m$^2$/g for later versions. These surfaces may contain pores having an average pore radius from 45 Angstroms to 100 Angstroms.

While the structure, surface area and pore size have imbued the nanoparticles with their protective properties, these structural features have also interfered with past attempts to incorporate the nanoparticles into tangible protective filter precursors. Failed attempts have resulted from an inability to control the van der Waals forces resulting in excessive clumping or from an inability to control the adhesive or retaining means resulting in occluding of useful surface areas or pores. The invention is concerned with products and methods that utilize nanoparticles in a flexible manner to readily incorporate one or more of their chemically adsorptive, chemically reactive or biocidally reactive properties.

Although illustrative embodiments of the present invention have been described herein, it is to be understood that the present invention is not limited to those precise embodiments, and that various other changes and modifications may be affected therein by one skilled in the art without departing from the scope or spirit of the present invention. For example, it is expressly intended that all combinations of those carbon beads, metal ions, nanoparticles and/or method steps and/or substrate materials which perform substantially the same function in substantially the same way to achieve the same results are within the scope of the invention. Moreover, it should be recognized that any disclosed form or embodiment of the invention may be incorporated in any other disclosed or described or suggested form or as a general matter of compatibility of application method. It is the intention, therefore, to be limited only as indicated by the scope of the claims appended hereto.

What is claimed is:

1. A method of protecting against a chemical or biological agent with a textile-based decontaminant, comprising the steps of:
   providing finely-divided metal-containing nanocrystals which possess protective properties and which cling together;
   aerating the nanocrystals with ionized air so that the nanocrystals become charged and therefor repel each other; and
   bonding the charged nanocrystals directly to the textile to non-occludingly retain the nanocrystal surface structure such that an interior of the textile is adapted to decontaminate chemical or biological agents disposed within a portion of the environment that encounters the interior of the textile.

2. The method of claim 1, wherein said textile includes spacer fibers that form a decontamination zone comprising nanocrystals having a BET multi-point surface area of at least about 1200 $m^2/g$.

3. The method of claim 2, wherein said bonding step comprises loading nanocrystals having an average pore radius from about 45 Angstroms to about 100 Angstroms onto said spacer fibers to obtain a predetermined chemical or biological decontamination capacity.

4. The method of claim 3, further comprising adjusting the length of said spacer fibers to control the distance through the decontamination zone.

5. The method of claim 4, further comprising adjusting the density of said spacer fibers to control the contact time with environments.

6. The method of claim 5, further comprising determining nanocrystal loading to obtain a target decontamination rate based on the distance and contact time of contaminants within the environment.

7. The method of claim 3, wherein said textile is an air-permeable textile having a vapor and liquid diffusion rate, wherein the diffusion rate is a function of one of textile thickness, size of spacer fibers, density of spacer fibers, configuration of spacer fibers and permeability of exterior layers.

8. The method of claim 7, further comprising determining nanocrystal loading to obtain a target decontamination rate as a function of the diffusion rates.

9. The method of claim 1, wherein the nanocrystals are formed from 1-200 nm sized nanoparticulate clusters.

10. The method of claim 1, wherein the nanocrystals include one of metal oxides, metal hydrates, metal hydroxides, and POMs.

11. The method of claim 1, wherein the nanocrystals are combined with a composition including one of a second different metal oxide, a reactive halogen atom, an alkali metal, a metal nitrate, $SO_2$, $NO_2$, and ozone.

12. The method of claim 1, wherein substantially no nanocrystals remain on the exterior of the layers.

13. A method of protecting against a chemical or biological agent with a textile-based decontaminant, comprising the steps of:
   providing a textile having finely-divided metal-containing nanocrystals which possess protective properties non-occludingly bound directly to the textile to retain the nanocrystal's adsorptive and reactive properties to decontaminate chemical or biological agents which encounter said interior of the textile; and
   exposing the textile to a chemical or biological threat such that the threat is reduced or eliminated as the threat enters the textile and encounter the jagged edge surface structure of the nanocrystals.

14. The method of claim 13, wherein said step of exposing includes rendering the chemical threat inert.

15. The method of claim 13, wherein said step of exposing includes subjecting biological agents within the textile to lysis.

16. The method of claim 13, wherein said step of exposing includes preventing biological entities from reproducing.

17. The method of claim 13, further comprising the step of incorporating the textile into clothing or textile products.

18. The method of claim 13, wherein following said step of exposing, the method further comprises the step of:
   reconditioning the textile by bonding additional nanocrystals to the textile with further non-occluding retaining means.

19. The method of claim 18, wherein said nanocrystals have a BET multi-point surface area of at least about 1200 $m^2/g$.

20. The method of claim 18, wherein said nanocrystals having an average pore radius from about 45 Angstroms to about 100 Angstroms.

21. The method of claim 13, further comprising the step of stacking a plurality of textiles to protect against a threat or multiple threats.

22. The method of claim 13, wherein following said exposing step, the method further comprises the step of:
   reusing the textile when the nanocrystals remain unconsumed during said exposing step.

23. The method of claim 13, wherein the nanocrystals are formed from 1-200 nm sized nanoparticulate clusters.

24. The method of claim 13, wherein the nanocrystals include one of metal oxides, metal hydrates, metal hydroxides, and POMs.

25. The method of claim 13, wherein the nanocrystals are combined with a composition including one of a second different metal oxide, a reactive halogen atom, a metal nitrate, $SO_2$, $NO_2$, and ozone.

* * * * *